US012183466B1

(12) United States Patent
Alchemy et al.

(10) Patent No.: US 12,183,466 B1
(45) Date of Patent: Dec. 31, 2024

(54) METHOD OF AND SYSTEM FOR IMPAIRMENT RATING REPAIR FOR THE MANAGED IMPAIRMENT REPAIR PROCESS

(71) Applicant: Alchemy Logic Systems Inc., Santa Rosa, CA (US)

(72) Inventors: John William Alchemy, Santa Rosa, CA (US); Bruce Brandon Wilson, Woodbury, MN (US); Jerry Lee Artz, St. Paul, MN (US)

(73) Assignee: Alchemy Logic Systems Inc., Santa Rosa, CA (US)

( * ) Notice: Subject to any disclaimer, the term of this patent is extended or adjusted under 35 U.S.C. 154(b) by 0 days.

(21) Appl. No.: 16/351,299

(22) Filed: Mar. 12, 2019

Related U.S. Application Data

(60) Provisional application No. 62/641,802, filed on Mar. 12, 2018.

(51) Int. Cl.
*G16H 50/30* (2018.01)
*G06F 17/18* (2006.01)
*G16H 50/70* (2018.01)

(52) U.S. Cl.
CPC ............. *G16H 50/30* (2018.01); *G06F 17/18* (2013.01); *G16H 50/70* (2018.01)

(58) Field of Classification Search
CPC ........ G16H 50/30; G16H 50/70; G06F 17/18; G06F 19/30; G06F 19/32; G06F 19/34;
(Continued)

(56) References Cited

U.S. PATENT DOCUMENTS 4,916,611 A    4/1990   Doyle, Jr. et al.
4,987,538 A    1/1991   Johnson et al.
(Continued)

FOREIGN PATENT DOCUMENTS

CA         2707207 A1    6/2009
WO    WO2008006117 A2    1/2008
(Continued)

OTHER PUBLICATIONS

Database. (2003). In B. Pfaffenberger, Webster's new World Computer Dictionary (10th ed.). Houghton Mifflin Harcourt. Credo Reference: https://search.credoreference.com/content/entry/webstercom/database/0?institutionId=743 (Year: 2003).*
(N.a.), "Physician's Guide to Medical Practice in the California Worker's Compensation System", 2016, State of California Department of Industrial Relations Division of Worker's Compensation, 4th ed., all pages. (Year: 2016).*
(Continued)

*Primary Examiner* — Christopher L Gilligan
*Assistant Examiner* — Jessica Marie Webb
(74) *Attorney, Agent, or Firm* — Haverstock & Owens, A Law Corporation

(57) ABSTRACT

A method and system addresses the circumstance where a lack of confidence in the impairment rating has arrested the impairment rating process and additional data collection is no longer possible. One or more incomplete data sets are compared to and corrected with a high accuracy database containing reviewed historical impairment data. An analysis of the data outputs a temporary impairment rating and a recovery score index, which yields a corrected and substantially accurate impairment rating report which can be used within the managed impairment repair process as the worker's compensation claim moves toward claim closure.

20 Claims, 4 Drawing Sheets

(58) Field of Classification Search
CPC ........ G06Q 50/00; G06Q 50/16; G06Q 50/22;
G06Q 50/24; G06Q 40/00; G06Q 40/07;
G06Q 40/08; G06Q 20/00; G06Q 20/10;
G06Q 20/22; G06Q 10/00; G06Q 10/06;
G06Q 10/10; G06Q 50/20–26
USPC ...................................................... 705/5, 2–4
See application file for complete search history.

(56) References Cited

U.S. PATENT DOCUMENTS

| | | | |
|---|---|---|---|
| 5,182,705 A | 1/1993 | Barr et al. | |
| 5,367,675 A | 11/1994 | Cheng et al. | |
| 5,517,405 A | 5/1996 | McAndrew et al. | |
| 5,544,044 A | 8/1996 | Leatherman | |
| 5,613,072 A * | 3/1997 | Hammond | G06Q 10/105 |
| | | | 705/35 |
| 5,778,345 A * | 7/1998 | McCartney | G16H 40/20 |
| | | | 705/2 |
| 5,911,132 A | 6/1999 | Sloane | |
| 6,003,007 A | 12/1999 | DiRienzo | |
| 6,065,000 A | 5/2000 | Jensen | |
| 6,604,080 B1 | 8/2003 | Kern | |
| 6,810,391 B1 | 10/2004 | Birkhoelzer et al. | |
| 6,865,581 B1 | 3/2005 | Cloninger, Jr | |
| 6,954,730 B2 | 10/2005 | Lau et al. | |
| 6,957,227 B2 | 10/2005 | Fogel | |
| 7,337,121 B1 * | 2/2008 | Beinat | G16H 50/50 |
| | | | 705/3 |
| 7,401,056 B2 | 7/2008 | Kam | |
| 7,440,904 B2 | 10/2008 | Hasan et al. | |
| 7,475,020 B2 | 1/2009 | Hasan et al. | |
| 7,509,264 B2 | 3/2009 | Hasan et al. | |
| 7,630,911 B2 | 12/2009 | Kay | |
| 7,630,913 B2 | 12/2009 | Kay | |
| 7,707,046 B2 | 4/2010 | Kay | |
| 7,707,047 B2 | 4/2010 | Hasan et al. | |
| 7,778,849 B1 * | 8/2010 | Hutton | G06Q 40/08 |
| | | | 705/3 |
| 7,813,944 B1 * | 10/2010 | Luk | G06Q 40/08 |
| | | | 705/4 |
| 7,870,011 B2 | 1/2011 | Kay | |
| 7,904,309 B2 | 3/2011 | Malone | |
| 7,930,190 B1 | 4/2011 | Milanovich | |
| 7,949,550 B2 | 5/2011 | Kay | |
| 7,970,865 B2 | 6/2011 | DeCesare et al. | |
| 8,019,624 B2 | 9/2011 | Malone | |
| 8,041,585 B1 | 10/2011 | Binns et al. | |
| 8,065,163 B2 | 11/2011 | Morita et al. | |
| 8,069,066 B2 | 11/2011 | Stevens et al. | |
| 8,185,410 B2 | 5/2012 | Brigham | |
| 8,301,575 B2 | 10/2012 | Bonnet et al. | |
| 8,346,573 B2 | 1/2013 | Glimp et al. | |
| 8,489,413 B1 | 7/2013 | Larson et al. | |
| 8,489,424 B1 | 7/2013 | Hasan et al. | |
| 8,510,134 B1 | 8/2013 | Sweat et al. | |
| 8,527,303 B2 | 9/2013 | Kay | |
| 8,615,409 B1 * | 12/2013 | McKown | G06Q 20/14 |
| | | | 705/2 |
| 8,630,878 B1 * | 1/2014 | Kravets | G06Q 40/08 |
| | | | 705/4 |
| 8,725,524 B2 | 5/2014 | Fano | |
| 8,725,538 B2 | 5/2014 | Kay | |
| 8,751,252 B2 | 6/2014 | Chamberlain | |
| 8,751,263 B1 | 6/2014 | Cave et al. | |
| 8,751,266 B2 | 6/2014 | Stang | |
| 8,775,216 B1 | 7/2014 | Amick et al. | |
| 8,864,663 B1 | 10/2014 | Kahn et al. | |
| 8,868,768 B2 | 10/2014 | Sokoryansky | |
| 8,888,697 B2 | 11/2014 | Bowman et al. | |
| 8,900,141 B2 | 12/2014 | Smith et al. | |
| 8,910,278 B2 | 12/2014 | Davne et al. | |
| 8,930,225 B2 | 1/2015 | Morris | |
| 8,959,027 B2 | 1/2015 | Kusens | |
| 8,954,339 B2 | 2/2015 | Schaffer | |
| 9,002,719 B2 | 4/2015 | Tofte | |
| 9,015,055 B2 | 4/2015 | Tirinato et al. | |
| 9,020,828 B2 | 4/2015 | Heidenreich | |
| 9,031,583 B2 * | 5/2015 | Pereira | H04L 67/306 |
| | | | 455/457 |
| 9,229,917 B2 | 1/2016 | Larcheveque | |
| 9,710,600 B1 * | 7/2017 | Dunleavy | G16H 15/00 |
| 11,461,848 B1 * | 10/2022 | Alchemy | G16H 10/60 |
| 11,625,687 B1 | 4/2023 | Alchemy | |
| 11,848,109 B1 | 12/2023 | Alchemy | |
| 11,853,973 B1 * | 12/2023 | Alchemy | G16H 40/63 |
| 11,854,700 B1 * | 12/2023 | Alchemy | G16H 50/20 |
| 2001/0027331 A1 | 10/2001 | Thompson | |
| 2001/0044735 A1 | 11/2001 | Colburn | |
| 2001/0053984 A1 | 12/2001 | Joyce | |
| 2002/0069089 A1 | 6/2002 | Larkin | |
| 2002/0077849 A1 | 6/2002 | Baruch | |
| 2004/0044546 A1 | 3/2004 | Moore | |
| 2005/0060184 A1 * | 3/2005 | Wahlbin | G06Q 40/02 |
| | | | 705/2 |
| 2005/0177403 A1 | 8/2005 | Johnson | |
| 2005/0256744 A1 | 11/2005 | Rohde | |
| 2006/0161456 A1 | 7/2006 | Baker | |
| 2006/0287879 A1 * | 12/2006 | Malone | G09B 19/00 |
| | | | 705/2 |
| 2007/0118406 A1 | 5/2007 | Killin | |
| 2007/0250352 A1 * | 10/2007 | Tawil | G16H 40/20 |
| | | | 705/4 |
| 2008/0046297 A1 | 2/2008 | Shafer | |
| 2008/0133297 A1 | 6/2008 | Schmotzer | |
| 2008/0154672 A1 * | 6/2008 | Skedsvold | G06Q 10/00 |
| | | | 705/7.15 |
| 2008/0183497 A1 | 7/2008 | Soon-Shiong | |
| 2009/0099875 A1 * | 4/2009 | Koenig | G16H 40/67 |
| | | | 707/E17.014 |
| 2010/0042435 A1 | 2/2010 | Kay | |
| 2010/0106520 A1 | 4/2010 | Kay | |
| 2010/0106526 A1 | 4/2010 | Kay | |
| 2010/0114609 A1 | 5/2010 | Duffy, Jr. et al. | |
| 2010/0217624 A1 | 8/2010 | Kay | |
| 2010/0240963 A1 * | 9/2010 | Brigham | G06Q 40/08 |
| | | | 600/300 |
| 2011/0077980 A1 | 3/2011 | Kay | |
| 2011/0077981 A1 | 3/2011 | Kay | |
| 2011/0145012 A1 | 6/2011 | Nightingale | |
| 2011/0161115 A1 | 6/2011 | Hampton | |
| 2011/0257919 A1 | 10/2011 | Reiner | |
| 2011/0257993 A1 * | 10/2011 | Shahani | G16H 10/60 |
| | | | 705/2 |
| 2011/0313785 A1 | 12/2011 | Lash | |
| 2011/0313912 A1 * | 12/2011 | Teutsch | G06Q 40/02 |
| | | | 705/38 |
| 2012/0022884 A1 | 1/2012 | Chillemi | |
| 2012/0102026 A1 | 4/2012 | Fortune | |
| 2012/0130751 A1 | 5/2012 | McHugh | |
| 2012/0232924 A1 | 9/2012 | Bingham | |
| 2012/0245973 A1 | 9/2012 | Pandya | |
| 2012/0278095 A1 | 11/2012 | Homchowdhury | |
| 2012/0280931 A1 * | 11/2012 | Stephanick | G06F 3/04883 |
| | | | 345/173 |
| 2012/0284052 A1 | 11/2012 | Saukas | |
| 2013/0024214 A1 | 1/2013 | Schoen et al. | |
| 2013/0132122 A1 | 5/2013 | Walsh | |
| 2014/0052465 A1 | 2/2014 | Madan | |
| 2014/0058763 A1 | 2/2014 | Zizzamia | |
| 2014/0073486 A1 * | 3/2014 | Ahmed | G16H 20/40 |
| | | | 482/9 |
| 2014/0136216 A1 * | 5/2014 | Beebe | G06Q 40/08 |
| | | | 705/2 |
| 2014/0172439 A1 | 6/2014 | Conway et al. | |
| 2014/0201213 A1 * | 7/2014 | Jackson | G06F 16/2228 |
| | | | 707/741 |
| 2014/0249850 A1 | 9/2014 | Woodson | |
| 2014/0278479 A1 | 9/2014 | Wang et al. | |
| 2014/0278830 A1 | 9/2014 | Gagne | |
| 2014/0303993 A1 | 10/2014 | Florian | |
| 2014/0379364 A1 | 12/2014 | Liu et al. | |
| 2015/0019234 A1 | 1/2015 | Cooper | |

(56) References Cited

U.S. PATENT DOCUMENTS

| | | | |
|---|---|---|---|
| 2015/0221057 A1 | 8/2015 | Raheja et al. | |
| 2015/0235334 A1 | 8/2015 | Wang et al. | |
| 2015/0242585 A1* | 8/2015 | Spiegel | G16H 10/60 705/2 |
| 2015/0278462 A1 | 10/2015 | Smoley et al. | |
| 2015/0286792 A1* | 10/2015 | Gardner | G06Q 40/08 705/3 |
| 2015/0324523 A1 | 11/2015 | Parthasarathy et al. | |
| 2016/0063197 A1* | 3/2016 | Kumetz | G06F 19/328 705/3 |
| 2016/0110334 A1* | 4/2016 | Yu | G06F 11/0769 715/223 |
| 2016/0125544 A1* | 5/2016 | Edwards | G06Q 10/1057 705/4 |
| 2016/0259499 A1* | 9/2016 | Kocienda | G06F 3/0483 |
| 2016/0283676 A1 | 9/2016 | Lyon et al. | |
| 2016/0292371 A1 | 10/2016 | Alhimiri | |
| 2017/0140489 A1 | 5/2017 | Ziobro | |
| 2017/0154374 A1* | 6/2017 | Iglesias | G06Q 40/08 |
| 2017/0177810 A1* | 6/2017 | Fulton | G06Q 40/08 |
| 2017/0228517 A1 | 8/2017 | Saliman | |
| 2017/0255754 A1 | 9/2017 | Allen | |
| 2017/0286389 A1* | 10/2017 | Ceneviva | G06F 40/106 |
| 2017/0316424 A1 | 11/2017 | Messana | |
| 2017/0352105 A1* | 12/2017 | Billings | G06Q 40/08 |
| 2018/0025334 A1* | 1/2018 | Pourfallah | G06Q 20/3223 705/41 |
| 2018/0279919 A1* | 10/2018 | Bansbach | A61B 5/45 |
| 2019/0065686 A1* | 2/2019 | Crane | G16H 10/60 |
| 2020/0126645 A1 | 4/2020 | Robbins | |
| 2020/0279622 A1 | 9/2020 | Heywood | |
| 2020/0286600 A1 | 9/2020 | De Brouwer | |
| 2022/0391993 A1* | 12/2022 | Alchemy | G06Q 40/08 |
| 2023/0196297 A1 | 6/2023 | Alchemy | |

FOREIGN PATENT DOCUMENTS

| | | | | |
|---|---|---|---|---|
| WO | WO-2016061340 A1 * | 4/2016 | | G06F 11/0706 |
| WO | WO-2018224937 A1 * | 12/2018 | | G16H 40/20 |

OTHER PUBLICATIONS

Programming languages. (2004). In W. S. Bainbridge (Ed.), Berkshire encyclopedia of human-computer interaction. Berkshire Publishing Group. Credo Reference: https://search.credoreference.com/content/entry/berkencyhci/programming_languages/0?institutionId=743 (Year: 2004).*

Park, Y., Butler, R. J. (2000). Permanant Partial Disability Awards and Wage Los. Journal of Risk and Insurance, 67(3), 331. Retrieved from https/dialog.proquest.com/professional/docview/769439682, Year 2000, 18 pages.

Rondinelli, Robert D., Guides to the Evaluation of Permanent Impairment, 2008 Sixth Edition, American Medical Association.

Cocchiarella, Linda and Andersson, Gunnar B. J., Guides to the Evaluation of Permanent Impairment, 2001 Fifth Edition, American Medical Association.

In B. Pffafenberger, Webster's new World Computer Dictionary (10th ed). Houghton Mifflin Harcourt, Credo reference:https://search.credoreference.com/content/entry/webster.com/database (year 2003).

American College of Occupational and Environmental Medicine, Occupational Medicine Practice Guidelines, 2004, Second Edition, OEM Press, Beverly Farms, MA.

Park, Y., & Butler, R. J. (2000). Permanent Partial Disability Awards and Wage Loss, Journal of Risk and Insurance, 67(3), 331, retrieved from https://dialog.proquest.com/professional/docview/769439682?accountid=142257 (Year: 2000).

Hakkinen, Arja, et al. "Muscle strength, pain, and disease activity explain individual subdimensions of the Health Assessment Questionaire disability index, especially in women with rheumatoid arthritis." Annals of the rheumatic diseases 65.1 (2006): 30-34. (Year: 2006).

"CA DWC Releases 4th Edition of Physician's Guide to Medical Practice in CA WC", Apr. 5, 2016, workcompwire.com, 7 pages.

Ammendolia C. Cassidy D., Steensta I, et al. Designing a Workplace Return-to Work Program for Occupational Low Back Pain: an intervention mapping approach. BMC Musculoskelet Disord. 2009;10:65. Published Jun. 9, 2009. doi: 10.1186/1471-2474-10-65 (Year; 2009). 10 pages.

Wasiak, Radoslaw, et al. "Measuring Return To Work." Journal of Occupational Rehabilitation 17.4 (2007): 766-781. (Year: 2007). 16 pages.

* cited by examiner

METHOD OF AND SYSTEM FOR IMPAIRMENT RATING REPAIR FOR THE MANAGED IMPAIRMENT REPAIR PROCESS

RELATED APPLICATIONS

This Patent Application claims priority under 35 U.S.C. 119 (e) of the U.S. provisional patent application, Ser. No. 62/641,802, filed on Mar. 12, 2018, and entitled "IMPAIRMENT RATING REPAIR FOR THE MANAGED IMPAIRMENT REPAIR PROCESS," which is hereby incorporated in its entirety by reference.

FIELD OF THE INVENTION

The present invention is generally directed to telemedicine. More specifically, the present invention is directed to a method and system for addressing the communication break down due to poor data resulting in failure of case closure in the existing worker's compensation claim process.

BACKGROUND OF THE INVENTION

An all too common and unfortunate occurrence in the worker injury claim and compensation process is a cessation of progression through the process from a lack of confidence by the stakeholders in the impairment evaluation. This lack of confidence can lead to litigation, delay and other problems regarding the necessary and required actions to obtain claim closure, and to prescribe a course of action to obtain maximum medical improvement (MMI). An improved impairment rating that satisfies stakeholder confidence can help move the injury claim forward to provide the injured worker appropriate care and compensation for the injury sooner. An incomplete impairment report currently requires a costly and lengthy independent review process.

An incomplete impairment report can result in a highly problematic situation for the stakeholders as the sources of an incomplete impairment report can be numerous. One common cause includes the unavailability of an originating physician or clinician to correct or update an initial impairment rating. In such cases, the treating physician or clinician may have relocated, retired or changed functions within the provider network.

Removing a critical part of the impairment rating process by removing an original physician or clinician or otherwise bringing about a stalemate can stop case progression. This can be particularly acute when the impairment rating is incomplete or contains errors. Stopping the impairment repair process can adversely impact all stakeholders.

The task of improving the value of impairment rating has several challenges. The doctor may not be familiar with the impairment rating process to execute and yield an adequate impairment rating, too much time has passed and/or the worker/patient medical pathology has changed. Additionally, there are medical and legal implications that can arise from a second impairment rating, particularly if the values are significantly different. This can exacerbate problems with the process even further by obfuscating the actual impairment resulting from the initial incident.

An impairment rating that has stalled or is incomplete or inaccurate can directly impact all stakeholders. Confusion arising from an inaccurate impairment rating can cause:

additional time spent for claim closure;
additional money for lawyers, courts and insurance companies;
more incorrect second opinions due to approach, experience and time from an original injury;
litigation;
unknown benefits owed to worker and costs to employer;
wide risk margin for claim underwriting by insurance companies; and
higher premiums for employers which are ultimately passed to society.

Consequently, a method and system that is able to accurately and confidently fill the gaps within the impairment rating process would be valuable to all stakeholders.

SUMMARY OF THE INVENTION

The present invention is directed to a method of and system for impairment rating repair for the managed impairment rating process. The method and system addresses the circumstance where a lack of confidence in the impairment rating has arrested the impairment rating process and additional data collection is no longer possible. One or more incomplete data sets are compared to and corrected with a high accuracy database containing reviewed historical impairment data. An analysis of the data outputs a temporary impairment rating and a recovery score index, which yields a corrected and substantially accurate impairment rating report which can be used within the managed impairment repair process as the worker's compensation claim moves toward claim closure.

In one aspect, a method of impairment rating repair comprises grouping injury impairment data into a cohort based on an injury type and an injury class. The injury impairment data is analyzed for one or more data anomalies. The injury data is compared to completed historical cohort data of a high accuracy database and based on that comparison, identifying one or more data gaps of the injury impairment data, augmenting the one or more data gaps based on the historical data to output corrected injury impairment data and outputting at least one of a tentative impairment rating and a recovery score index based on the corrected injury impairment data. In some embodiments, the method comprises reviewing the tentative impairment rating and the recovery score index for accuracy. In some embodiments, if the corrected injury impairment data, the tentative impairment rating and the recovery score index are accurate, the data is transferred to the managed impairment rating process. Alternatively, if the corrected injury impairment data, the tentative impairment rating and the recovery score index are not accurate, then the data is further scrutinized to fill any remaining inaccuracies and gaps. In some embodiments, the method comprises assigning a statistical level of confidence for the corrected injury impairment data for each corrected data gap. In some embodiments, the injury type and the injury class are based on one or more administrative rule sets as applied to the injury impairment data. In further embodiments, the method comprises identifying the breakdown within the impairment rating. In some embodiments, a high accuracy database is populated according to complete, scrutinized and correct impairment data sets.

In another aspect, a method of impairment rating repair comprises populating a high accuracy database with complete, scrutinized and correct impairment data sets, comparing the populated data sets to one or more incomplete impairment data sets, based on the comparison of the populated data sets and the incomplete impairment data sets, identifying one or more data gaps and filling the data gaps based on the populated data sets to obtain corrected injury impairment data. In some embodiments, the method comprises outputting at least one of a tentative impairment rating and a recovery score index. In some of these embodiments, the method comprises reviewing the tentative impairment rating and the recovery score index for accuracy. In some embodiments, if the corrected injury impairment data, the tentative impairment rating and the recovery score index are accurate, the data is transferred to the managed impairment rating process. In further embodiments, the method comprises assigning a statistical level of confidence for the corrected injury impairment data for each corrected data gap. In some embodiments, the one or more incomplete impairment data sets are grouped into a cohort based on an injury type and an injury class. In some of these embodiments, the injury type and the injury class are based on one or more administrative rule sets as applied to the one or more incomplete impairment data sets.

In a further aspect, a system for impairment rating repair comprises an incomplete data set input and a high accuracy database. The incomplete data set sends information to the high accuracy database. In response, the high accuracy database corrects the incomplete data set and outputs at least one of a temporary impairment rating and a recovery index score based on a comparison of the incomplete data set with one or more correct impairment data sets. In some embodiments, the tentative impairment rating and the recovery score index are reviewed for accuracy. In some embodiments, if the corrected injury impairment data, the tentative impairment rating and the recovery score index are accurate, the data is transferred to the managed impairment rating process. In some embodiments, a statistical level of confidence for the corrected injury impairment data is assigned. In some embodiments, a high accuracy database is populated according to complete, scrutinized and correct impairment data sets.

In still a further aspect, a system for impairment rating repair for the impairment rating process comprises a computing device configured for inputting one or more impairment rating data sets, a high accuracy database for receiving the one or more impairment rating data sets and a processor for analyzing the one or more impairment rating data sets for missing and incorrect data based on an injured worker's pathology, wherein the high accuracy database supplements the missing and incorrect data of the one or more impairment rating data sets to output one or more correct impairment data sets. In some embodiments, the high accuracy database is populated according to complete, scrutinized and correct impairment data sets.

DETAILED DESCRIPTION OF THE EMBODIMENTS

Figure 1:
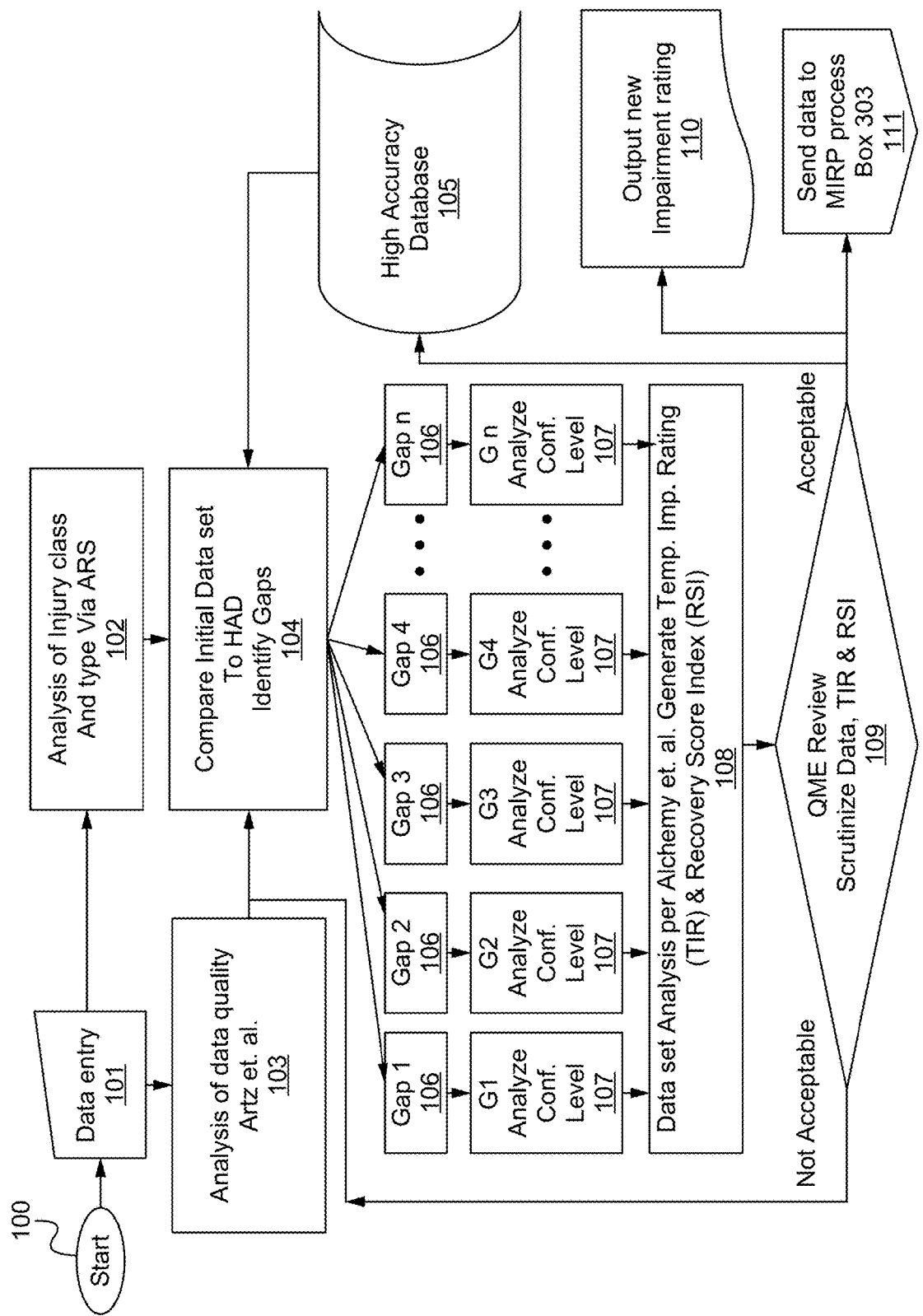
FIG. 1 illustrates a method of impairment rating repair in accordance with some embodiments.

The logic structure provided for analyzing an injured body region; that includes but is not limited to The American Medical Association's (AMA) Guide to the Evaluation of Permanent Impairment or federal or state mandates, US Social Security, the VA Medical Center system, or any other national or international set of administrative rule sets. This unique incorporation of a diversity of ARSs, particularly when multiple body parts are simultaneously involved, provides a basis for a very complex and robust interaction in the rating process. For this reason, the Rate Fast algorithms incorporate a diversity of ARSs in them. The diversity of ARSs, in a clinical 'pencil and paper, process is the primary source of impairment rating error. For a clinician to be aware of all the ARSs and their interactions, in a time constrained clinical setting makes it virtually impossible to achieve accurate, reproducible ratings without a governing algorithm. Shell Program: Includes but is not limited to the following functions:

Controls the graphic user interface guiding the user through the data collection and entry process, and automatically alerts the user when a "real time" collection of data results in a non-valid calculation required by the ARS. Collects both user-related information and claim data sets entered by the user. Places a "thin client" program on the user's internet-connected computing device to facilitate user input. Encrypts and passes user and claims data sets to the database controller for storage.

A user accesses the RateFast program with an electronic device and connects to the internet to create a user data set within the RateFast main frame. In some embodiments, the server model code software utilizes a redundant array of computer servers on which the majority of the software runs (user interface, calculation engines, etc.) A second array of redundant servers allows storage and indexing of user and claim data set. A user can access software through internet connected computer devices and secured login methods. In some embodiments, a small portion of software runs on the user's computing device. This enables software to more efficiently access the RateFast main frame data and improves performance. Alternatively, the software can be stored and operated on the user's device. In this alternative, the data taken in the exam can also be stored locally.

After the complete claim data set has been entered, it is encrypted and transferred over the internet to the RateFast servers. The clinical data set is decrypted and then analyzed by a calculation process specific to the injured body region and the ARS as chosen by the user. This process can include, but is not limited to an internal consistency check to ensure congruency within a clinical data set (e.g. physical examination findings of a right shoulder injury should correlate with imaging findings on the right shoulder). Congruency within the CDS reduces the opportunity for error and also allows stakeholders to verify the accuracy of the report with independent validation. Impairment values are assigned according to the ARS. Within any given administrative rule set, there is a wide variety in scope and complexity for the criteria applied to any given body part. For example, an elbow is evaluated using different criteria than a knee. The impairment values are subjected to the hierarchy of impairment processes, and a single number, whole person impairment rating is generated.

The RateFast system comprises three separate and interconnected processes. The system comprises a shell, a database controller and an impairment rating calculator. The RateFast shell connects to an electronic device, such as described above and controls a graphical user interface that guides a user through the data collection and entry process described above. In some embodiments, the RateFast shell also alerts the user when a "real time" collection of data results in a non-valid calculation required by the ARS. The shell collects both user-related information and claim data sets entered by the. The RateFast shell is also able to communicate with the electronic device to place a "thin-client" program on the device to facilitate the user input. The RateFast shell also encrypts the user inputted data and passes the claims data sets to the database controller for storage.

The database controller stores, indexes, and retrieves all user and claim data sets and any calculations performed on those data sets. The data sets are received at the impairment rating calculator, which comprises a set of spreadsheets into which the clinical data sets are imported and subject to the hierarch of impairment, such as described above. After an impairment rating is calculated, the clinical report is encrypted and sent to the user and the electronic device.

Shell logic manages the collection of the administrative rule set (ARS) and the clinical data set (CDS) within the RateFast system. Type 1 shell logic performs validation calculations at the level of the user interface. For example, in some embodiments, clinical data is validated by the analysis of the appropriate ARS and instructing if additional CDS is needed. This logic prompts the user to enter additional physical exam findings and to expand the clinical data set if it is required by the administrative rule set. The shell logic either expands the existing clinical data set with simply more data or creates an additional set of data by prompting another unique physical activity.

During the collection of the CDS, the ARS interrogates the CDS for anomalies including but not limited to similar values outside of the expected data range. In this manner, the CDS can properly be interpreted as authentic and not otherwise synthesizes. The shell logic optimizes the user's time by prompting only for clinical data as necessary for the final production of a specific impairment report. Additionally, the method provides the added benefit of standardization of the content impairment reports that otherwise might contain either extraneous information or have omitted information necessary of a correct impairment rating calculation.

Type 2 shell logic (nested) can drive, but is not limited to the clinical data set collection sequence. For example, the presence or absence of medication and clinical side effects if present, can allow additional assignment of impairment ratings based on the CDS and based on the treatment burden and/or sustained side effects as a consequence of permanent ongoing treatment.

The application of the ARS to the specific injury has with it, an associated algorithm. Hence, extensive logic is contained within the impairment calculators, which are separate from the shell program. Data entered via the shell is imported into data fields in calculator, then applied to criteria defined by the ARS to determine a return value, if any. Once a complete set of return impairment values has been determined for all criteria defining impairment, those values are subject to the additional calculations to determine a final impairment rating for a specific body part.

As described above, the composition of statistical modeling, pattern recognition, feedback to clinician, data retention and self-reporting method to assure accuracy and integrity to the final impairment rating. In operation, the method that teaches unique applications of statistical analysis to medical processes in order to assist in obtaining substantially improved accuracy of impairment ratings. This analysis is comprised of multiple components. First, a statistical model, evaluates the input data for anomalies or outliers. If none are found, the data proceeds into the impairment calculator. Second, an analysis for patterns in the data, which fall within the expected range, will also trigger an anomaly response. When an anomaly response is triggered, the clinician is queried as to the validity of the data just entered. Simultaneously, HIPPA compliant stakeholders retain the initially entered data for possible later audit.

The statistical model can be chosen based on its ability to accurately represent the historical medical data and assess the input data for patterns. Also, other numerical properties are extracted from the historical data. The model and related numerical properties are then used to evaluate the input data while the clinician is entering it. This 'real time' evaluation of the input data enables virtually immediate identification of patterns or values that deviate significantly from the expected ranges and their variability, i.e. abnormal data. These abnormal data, whether their origin is purposeful fraud, a mistake on behalf of an Examiner, equipment malfunction or just natural aberration, are noted and left for further review by the clinician and other parties. Hence, this analysis performs as an audit and feedback of the data quality to the clinician to assist in managing the integrity of the input data during the examination process to attain an accurate impairment rating.

Embodiments of the invention are directed to a method and system that addresses the circumstance where a lack of confidence in the impairment rating has arrested the impairment rating process and additional data collection is no longer possible. One or more incomplete data sets are compared to and corrected with a high accuracy database containing reviewed historical impairment data. An analysis of the data outputs a temporary impairment rating and a recovery score index, which yields a corrected and substantially accurate impairment rating report which can be used within the managed impairment repair process as the worker's compensation claim moves toward claim closure.

Reference will now be made in detail to implementations of a method of and system for impairment rating repair for the managed impairment repair process. The same reference indicators will be used throughout the drawings and the following detailed description to refer to the same or like parts. In the interest of clarity, not all of the routine features of the implementations described herein are shown and described. It will be appreciated that in the development of any such actual implementation, numerous implementation-specific decisions can be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Most states share a common worker's compensation processes and methods. A report by the State of California Department of Industrial Relations analyzed the worker's compensation claim process in the state of California. ["Physician Reporting Requirements for Injured Workers in California," © Rand Corp., Santa Monica, CA (2017), hereby incorporated by reference in its entirety] The report summarized the numerous opportunities for breakdown and causes of problems in the worker injury claim process. However, this report failed to consider two critical solutions. One, the existence of a central driver or "policeman" and two, the preponderance of cases that stall due to incomplete and/or inaccurate impairment ratings. The method and system such as described below addresses the second question, how to correct incomplete and/or incorrect reports to enable stakeholder confidence to move the claim forward to claim closure.

Performing an impairment rating requires a highly skilled person to execute the impairment rating process, minus a guided algorithm. Typically, this person is more than a general practicing physician, and is often a qualified medical examiner (QME). A QME is a distinct minority, even among clinicians and physicians. The specialty training of a QME provides an intellectual capacity to the examination process. A QME with specific talents such as this is a 'subject matter expert' or as known in the field of medical practice as a 'knowledgeable observer.

Obtaining an improved impairment rating that satisfies stakeholder confidence is necessary to move the worker's compensation claim forward. In some embodiments, this can be achieved by applying a statistical analysis of an initial impairment examination data in conjunction with an application of strict administrative rules sets (ARSs) as to the type and number of pathologies present and by complementing the initial data set by comparison to a high accuracy database (HAD), which is complete and class adjusted to address potential gaps within the initial data set. The combination of these methodologies yields an impairment rating with substantially higher quality values and better representing the initial worker pathologies. This methodology can help establish improved confidence in the stakeholders that is sufficient to restart the impairment repair process.

This system and method enables the stakeholder such as workers, employers, insurers, medical providers, the judiciary and others to reach an agreement on the necessary and needed course of action(s) to complete the impairment repair process and to close the compensation claim. This method also addresses the flaw in the impairment repair process that while a rule set for an adjudication is present, there is no driver or "policemen" of the process.

The present invention repairs existing gaps in the impairment rating process and restores the data set to a point at which stakeholder confidence in the claim basics, such as the impairment rating enables the process to move forward. As stated above, the present invention does this by the application of appropriate ARSs on the reported pathologies present as well as a second screening using the HAD. This comparison to a historical data set reveals data gaps that when filled can yield an impairment rating that has a high likely hood for substantial accuracy improvement. Frequently, the improved accuracy rating also leads to improved confidence of the stakeholders resulting in a restarting of the impairment rating repair process moving toward claim settlement.

The present invention addresses those situations where the impairment rating process has broken down due to confusion arising from an incomplete, inaccurate or dubious impairment rating. There are numerous reasons why the workers claim may stall and consequently there is an ongoing iteration between the stakeholders: employee, employer, insurance company, health providers, clinics, worker's compensation judge and other without any true progress to completion. This lack of closure is detrimental to all interested stakeholders.

Additionally, because the impairment rating and/or the data set for the injured worker is incomplete, the worker may not be receiving the appropriate treatment for the type, scale, and/or scope for the actual medial pathology present. The time delay can also create a risk in obtaining the best maximum medical improvement (MMI) for the worker's pathology and extend the scope of the worker's compensation claim in the worker's life.

Further, because the employer may be without the worker during the impairment repair process, an employer must higher an additional worker or enduring a loss of function for the organization. If the employer is self-insured (meaning the direct cost of the process and the claims are paid by the employer) then operating funds need to be set aside for the duration of the claim while the actual costs are realized. The holding of operational capitol such as this directly competes with the health of the organization.

Insurance companies will benefit from a claim closure as well. Ongoing, non-closure of claims can diminish the brand value of the insurance administrator to its customers, resulting in decreased reputation and business.

Health providers, clinics and physician's goals are to assess, provide treatment and obtain the best possible outcome for their patients. Having incomplete or inaccurate impairment assessment at the beginning of the impairment repair process significantly jeopardizes this desired outcome. Executing therapies using an inaccurate data or an inaccurate diagnosis can lead to adverse and unexpected outcomes.

The worker's claim judiciary, lawyers and legal staff spend time on a case where there may frequently be an overwhelming case load. Unimpeded claim processing enables a prudent closure rate which saves public resources and allows those resources to be available and be more efficiently used for societal benefit.

As described above, the method and system inspects, compares, and corrects an initial data set in an accurate context for an injured body part based on the injury and a severity of the injury.

Some examples are shown below. These examples are in no way meant to limit the scope of the invention but rather illustrates some specific situations to exhibit the present invention. The method and system as described herein is applicable to any appropriate scenario such as attributed to a stalled worker's compensation claim.

Example 1

A 45-year-old woman who works as a housekeeper in a rural area falls from a ladder and injures her right knee on the job. She fails to respond to conservative treatment. The injury requires a total knee replacement.

After the surgery and a period of recovery, she goes back to work on modified duty. This modified duty includes a work restriction on kneeling and bending the knee. Hence, the employer cannot ask her to kneel or perform other activities that are strenuous on her knee. However, these tasks are considered a basic requirement of the job description.

Consequently, the employer must make a "temporary accommodation" for the worker by giving her modified work duty. Approximately half of the job description, or twenty hours per week of modified work duty is all that is available for her to perform per week, leaving half of the job description needs unmet.

During this time of convalescence, the employer must hire a second worker to perform the remaining half of the job needs. The hiring of a second worker creates additional expense due to overhead costs including: administration, social security, medicare and medicaid taxes, etc. The insurance carrier also incurs an expense as it pays the first worker for the extra hours per week that she is unable to work.

Eventually, the surgeon determines that the worker's knee functionality has improved and no further gains are anticipated. This means that the injury has reached the point of MMI, and it is now time to determine the worker's permanent impairment and for a final claim settlement. This final impairment rating is what the worker compensation board will use to determine what economic offsets are necessary, concluding the workers" compensation claim. However, there are no qualified physicians in the rural area who are able to perform a final impairment report.

The stakeholders, lacking a final impairment rating report, cannot determine permanent loss. Thus, the stakeholders cannot determine the worker's entitlement to benefits, or functional accommodations to return to work. The employer cannot legally 'let her go' until such time that there is a final impairment report.

In summary, the stakeholder's situations below reflect the set of circumstances that arise from a claim lacking closure. Hence, they are "left in a state of limbo":

The housekeeping agency only has half of an employee, and the business incurs expense by hiring another worker to pick up the slack. In addition, the agency, if self insured, needs to keep money set aside in the circumstance the case is actually settled.

The injured worker lives with the uncertainty that she'll be able to keep her job, and without receiving any benefits associated with permanent disability.

The insurance administrator spends time struggling to close the claim and spend resources compensating the injured worker for the hours she cannot work.

The case remains open in the Workers Compensation Board docket indefinitely.

After many unsuccessful attempts to find a provider in the area to perform an impairment rating, the claim remains open after three years. This is in violation of California statutes, as there must be an impairment report within twenty days of the injury being declared MMI, in this case MMI by the surgeon. Many other states have similar legislation regarding the timing of case closure.

Example 1: Solution

At the time the surgeon claimed MMI, the injured worker's claim documentation is entered into the presently described system. This includes the medical data in the chart, the patient's demographics, the treatments that were used to treat the injury, and if the chart is thorough, measurements include the patient's knee's functionality.

The system then automatically performs a data analysis on the patient's chart. This can comprise an analysis of the data for completeness against the HAD, an analysis of statistical anomalies, inserting data into identified gaps based on the HAD, creating a recovery score index (RSI) and outputting a temporary impairment rating (TIR). The system also obtains input from a QME or qualified observer. If the TIR is correct then the system creates a final impairment rating report, stores the reviewed data and sends data to the managed impairment repair process. The final product is a final impairment rating report for the patient, based on the patient's original claim, with data gaps augmented by use of the HAD.

Thus, this claim that has been left open for a prolonged period of time can be provided an enhanced quality impairment rating value and report enabling the claim to proceed to closure.

Example 1: Conclusion

The above example of a non-existing resource for the filing of an impairment report is a highly problematic situation for all stakeholders. However, the application of appropriate ARSs, such as described above, on the reported pathologies present combined with a second screening of the data set comparing it to a historical data set yields an impairment rating that has a high likely hood for substantial accuracy improvement. This improved accuracy impairment rating leads to improve confidence by the stakeholders and can result in restarting the impairment repair process, including case closure by the workers compensation board.

Example 2

Case 2 is an example of the present invention as applied to a remote location. This case shows a telemedicine example. The case has been established and follow up treatment not available (No PR2, PR4).

A 34-year-old male strains his back lifting a post on a construction site. He is seen at a local rural emergency room (ER). He has 7/10 constant bilateral leg pain and cannot sit, stand or walk beyond 15 minutes. He cannot lift more than 10 lbs. (4/34 ADLs impacted). An X-ray shows L4-S1 mild degenerative changes. A doctor's first report (DFR) is filed and he is placed on modified duty and provided medication. He is told to follow up with a primary treating physician in the worker's compensation system and released. The worker and his employer discover there are no insurance network providers within a 75 mile distance. There is no qualified medical provider available for impairment rating to assign claim value. No further care is available.

Example 2 Solution

The case is at stalemate after three months. The initial ER visit (DFR) is class matched for RSI severity and a historical data set impairment report is created. The ratable data set returns an impairment value of 1% Whole Person Impairment (WPI) for multilevel degenerative changes and 3% WPI for neurogenic leg pain. The high accuracy data set class rating provides an additional 3% WPI for ratable loss of motion and 1% for motor weakness. Final HAD class rating is determined to be 8% WPI. A claim settlement is provided and the worker is provided a future care settlement award and he obtains local care at a primary care health plan clinic. He is returned to work in 6 months.

Example 3

This example of the invention is an application early in the process. In Case 3, the initial impairment report is found that the worker has achieved MMI and rated by Primary Treating Physician (PTP) but there are obvious flaws in the documentation. The critical issue is lack of stakeholder confidence due to the obvious errors in the final impairment report.

A 52-year-old female injured her right shoulder doing repetitive work. She files her DFR with her PTP and treatment with imaging follows. Her X-ray shows mild glenohumeral arthritis and moderate AC joint arthritis. She is sent to orthopedics and found to be non surgical. Her PTP determines her to be MMI. The PTP serves the stakeholders a permanent impairment report. She is experiencing 4/10 pain level. No frequency of the pain is provided. No ADL inventory is documented. Exam documents no ranges of motion, no neuromotor exam (a.k.a. Rang Of Motion or ROM). She is provided permanent functional limitations for no lifting >10 lbs. An impairment exam of 0% WPI is determined by the PTP. No apportionment is (0%) is determined. No future care is mentioned in the report. She is released from care. The patient receives a letter from the insurance 6 weeks later informing her that her claim is closed and her settlement value is $0.

The worker obtains an attorney and the claim costs are now increased by $25,000. An Agreed Medical Exam (AME) is ordered adding an additional $5000 to the claim costs. This case is still open at two years following attorney representation. She selected another PTP and the case transfer fees increased the claim costs an additional $5000.

Example 3 Solution

The case has been erroneously closed by the PTP and resulted in the insurance carrier offering an incorrect settlement and benefit package. The ratable data set is extremely poor in quality. The Invention algorithm analysis reveals a data gap of 66%, which is an "F" quality data set. The worker perceived she had no choice but to obtain representation to protect her rights. The result for this obvious incorrect impairment report by the PTP was a) increased litigation b) delay in case closure c) additional costs for transfer of care seeking an competent PTP, and d) additional costs for an AME to repair the impairment exam.

This case scenario may have been avoided using the present invention. In application of the presently described system, her recovery score index cohort is found to be 4, which is mild/moderate injury severity. The pain frequency is determined to be 75% with an ADL loss of 4/34 activities. The Range of Motion (ROM) loss adjusted for <10% variance with the uninjured side serving as an impairment baseline is determined to be 4% WPI and neuromotor exam findings 0% WPI. Apportionment is determined to be 22%. Future care is determined to include medications, therapy, injections, durable medical equipment (theraband kits), access to surgeon and imaging. This permanent impairment value results in a ratable loss settlement of $9,000 and a lifetime medical award with a compromise and release value of $45,000.

Had the present invention been initially applied to this case, when there was broad stakeholder recognition that the initial data set was incorrect, the two years of litigation, pain experienced by the worker and dwell time to obtain appropriate therapy for improvement, court and doctor fees etc. could have been avoided. In addition, the self insured employer would not have needed to set aside the potential claim costs, from the core business needs, for an additional two years. As a result, the seemingly more expensive costs of the re-evaluation and adjudication at the case closure would have been more than offset by repairing the initial data set and impairment rating.

Referring now to FIG. 1, a flow chart illustrating a method of impairment rating repair for the managed impairment repair process is depicted therein. The method such as shown within FIG. 1 implements one or more algorithms such as described within U.S. patent application Ser. No. 14/996,067 to Alchemy et al. (the '067 Application), which is hereby incorporated by reference in its entirety and the '581 Application. In some embodiments, the data is then analyzed such as described within U.S. patent application Ser. No. 16/124,960 to Alchemy et al. (the '960 Application), which is also hereby incorporated by reference in its entirety. As explained in the '067 Application, an incomplete impairment rating exam entered, if not corrected, are carried forward in an impairment rating process, in which errors can translate into larger issues over time. As such, it is important to identify any data gaps in an original data set for correction. The method such as shown in FIG. 1 can reveal one or more data gaps which may be present within an original data set.

As described within the '067 Application, algorithms are used to guide the measurement of the examinee's pathology resulting from an injury. Pathology as defined herein for the purposes of this document includes, but is not limited to a loss, loss of use or derangement of any body part, organ system, or organ function as these concepts are defined by the AMA Guides 5$^{th}$ Ed. page 2 or similar definitions set forth in previous and subsequent editions. The application of this set of methods provides highly accurate and reproducible Impairment Ratings for Workers Compensation claims. This begins with use of proper measurement methods and data acquisition. This objective data set is used to perform established, unique and proprietary analysis that provides reproducible results. These methods enable a broad range of Examiners to perform such ratings and attain much more precision in the rating outcome with little or no variation across jurisdictions, clinics, and geographies.

The method also uses algorithms that can be accessed via a computer, laptop, tablet and smart phone app. The algorithms guide the Examiner to perform specific tests to ascertain the strength, range of motion, and pain present in the examinee. Pain is defined herein for the purposes of this document to include, but is not limited to pain and/or symptoms resultant from an injury. The Examiner is provided a step-by-step menu for the data generation and documentation process. Entering the data into the algorithm results in several unique simultaneous responses, depending on the number and nature of injuries, body part(s), value range of data entered. Body part(s) is defined herein for the purposes of this document to include but is not limited to body part(s) and/or organ systems. The data is evaluated for variance and possible anomalies in the data. The methods also store measurements for later calculation and use and/or select appropriate protocols (or Administrative Rule Sets-ARS), and perform calculations among which can be a partial or Whole Person Impairment rating.

The wide diversity of examination protocols resulting from the different body parts imposes a vast array of different interactive protocols. This is particularly cumbersome when multilateral injuries\ pathologies are present simultaneously. Hence, the distinct different protocols (or "Administrative Rule Sets"-ARS) requires each body part to have it's own unique algorithms. Examples of body parts, representing different and unique algorithms, are: the spine, upper extremities, lower extremities, skin, pain, etc. Because of the wide range of protocols and resulting unique algorithms, the Examiner is faced with a myriad of decisions in the clinical setting, in addition to the performance of the exam itself. This complexity is a significant source of the errors and variability in the impairment rating process. Having these ARS's predetermined enables the clinical evaluation to target the appropriate tests and measurements, eliminating error and reducing variability in the impairment rating process.

Currently, the AMA guides call for the various portions of the body to be evaluated differently. Each body part has it's own unique characteristics to be examined. This results in each body part having a different Administrative Rule Set and resulting algorithm. In addition, another uniquely complex algorithm set that manages the interaction between the body part algorithms.

Nine different unique algorithms make up this invention, including: RateFast HUB, The Upper Extremity, The Lower Extremity, The Spine, Skin, Variable Thread Analytic Computation (VTAC), Maximal Medical Improvement (MMI), Calculator tool, Almaraz-\Guzman, Cannon v. the City of Sacramento, AMA Guides 5th Ed. Section 1.20% Whole Person, Apportionment. Chapter 18 Pain AMA Guides 5th Ed. Calculator and Comparison of Methods or similar conceptual definitions set forth in previous or subsequent AMA Guides Editions, and Comparison of Methods.

The logic structure provided for analyzing an injured body region; that includes but is not limited to The American Medical Association's (AMA) Guide to the Evaluation of Permanent Impairment or federal or state mandates, US Social Security, the VA Medical Center system, or any other national or international set of administrative rule sets. This unique incorporation of a diversity of ARSs, particularly when multiple body parts are simultaneously involved, provides a basis for a very complex and robust interaction in the rating process. For this reason, the Rate Fast algorithms incorporate a diversity of ARSs in them. The diversity of ARSs, in a clinical 'pencil and paper, process is the primary source of impairment rating error. For a clinician to be aware of all the ARSs and their interactions, in a time constrained clinical setting makes it virtually impossible to achieve accurate, reproducible ratings without a governing algorithm.

Shell logic manages the collection of the administrative rule set (ARS) and the clinical data set (CDS) within the RateFast system. Type 1 shell logic performs validation calculations at the level of the user interface. For example, in some embodiments, clinical data is validated by the analysis of the appropriate ARS and instructing if additional CDS is needed. This logic prompts the user to enter additional physical exam findings and to expand the clinical data set if it is required by the administrative rule set. The shell logic either expands the existing clinical data set with simply more data or creates an additional set of data by prompting another unique physical activity.

During the collection of the CDS, the ARS interrogates the CDS for anomalies including but not limited to similar values outside of the expected data range. In this manner, the CDS can properly be interpreted as authentic and not otherwise synthesized. The shell logic optimizes the user's time by prompting only for clinical data as necessary for the final production of a specific impairment report. Additionally, the method provides the added benefit of standardization of the content impairment reports that otherwise might contain either extraneous information or have omitted information necessary of a correct impairment rating calculation.

Type 2 shell logic (nested) can drive, but is not limited to the clinical data set collection sequence. For example, the presence or absence of medication and clinical side effects if present, can allow additional assignment of impairment ratings based on the CDS and based on the treatment burden and/or sustained side effects as a consequence of permanent ongoing treatment.

The application of the ARS to the specific injury has with it, an associated algorithm. Hence, extensive logic is contained within the impairment calculators, which are separate from the shell program. Data entered via the shell is imported into data fields in calculator, then applied to criteria defined by the ARS to determine a return value, if any. Once a complete set of return impairment values has been determined for all criteria defining impairment, those values are subject to the additional calculations to determine a final impairment rating for a specific body part.

The method such as shown in FIG. 1 can reveal one or more data gaps which may be present within an original data set.

The method begins in the step 100. In the step 101, data from an incomplete impairment rating exam is entered. The data is then analyzed for injury class and type in the step 102. In some embodiments, the data set is analyzed for injury class and type. The data as entered in step 101 is also analyzed for statistical anomalies in the step 103. The process outputs of the step 102 and 103 are then output and combined in the step 104 and the combined data is compared according to data within a populated a high accuracy database. The method then proceeds to an appropriate prioritization of pathologies and apportionments ad also identifies the initial data set for completeness.

An appropriately complete set for an impairment rating has specific types of sub sets of data, such as range of motion (ROM), activities of daily living (ADL), and others that should be included. If one or more of these data sets are not present, then the one or more gaps are identified in the step 106. Based on the patient and injury information, the patient is assigned a class standard cohort of similar claims based on historical data of the HAD to be used for statistical data modeling and augmentation of the data gaps as identified in the step 106. The data gaps can be corrected and filled according to data of the high accuracy database, which has been reviewed and scrutinized for completeness and class adjusted based on similar prior claims.

Based on each data gap as identified in the step 106, a statistical level of confidence for each corrected data gap/result is assigned in the step 107. The confidence level is based on an accumulation of the numbers of reports of the injured worker's cohort, such as described above. The more available historical data in the high accuracy database, the higher the statistical confidence level of step 107.

Then, in the step 108, the corrected data is coalesced to generate a TIR. Additionally, based on a comparison of the data sets and an original patient chart with the coalesced data, a RSI is also generated. The TIR is an intermediate output which reapplies the ARSs such as described above, to the original data with the data gaps corrected/filled. The TIR is then analyzed by a further comparison to the historical data within the high accuracy database. The historical data within the HAD has previously been subject to the one or more ARSs.

In the step 109, the corrected data, TIR and RSI including the type and class of injury are reviewed. If this interim data is acceptable, then the TIR is output as a new impairment rating for the injury in the step 110 and the data can be transferred and used for the managed impairment repair process (MIRP) in the step 111, such as described within the '581 Application. If however, the interim data is unacceptable, then it is further scrutinized and compared according to a HAD such as described at step 104, above. In some embodiments the data is reviewed by a QME, knowledgeable observer or other subject matter expert. The method ends in the step 112.

In some embodiments, when data from an incomplete impairment rating is presented incomplete and without context of examination method of completeness, the data undergoes an additional analysis such as described within the '067 Application. This analysis determines the nature of the examination and where the examination process broke down to identify gaps and discrepancies with typical or normally expected values. This analysis can also identify the presence of potential anomalies within the original data set. The output of this process can be analyzed within the method, such as described above, and reviewed such as described within the step 109.

Case transfer to the MIRP, in the step 111 is an additional function of the present invention which assists moving a claim toward closure by adding stakeholder oversight, and enabling prudent claim closure. The output of step 111, such as described above represents the claim transfer to the MIRP, such as described within the '581 Application.

Figure 2:
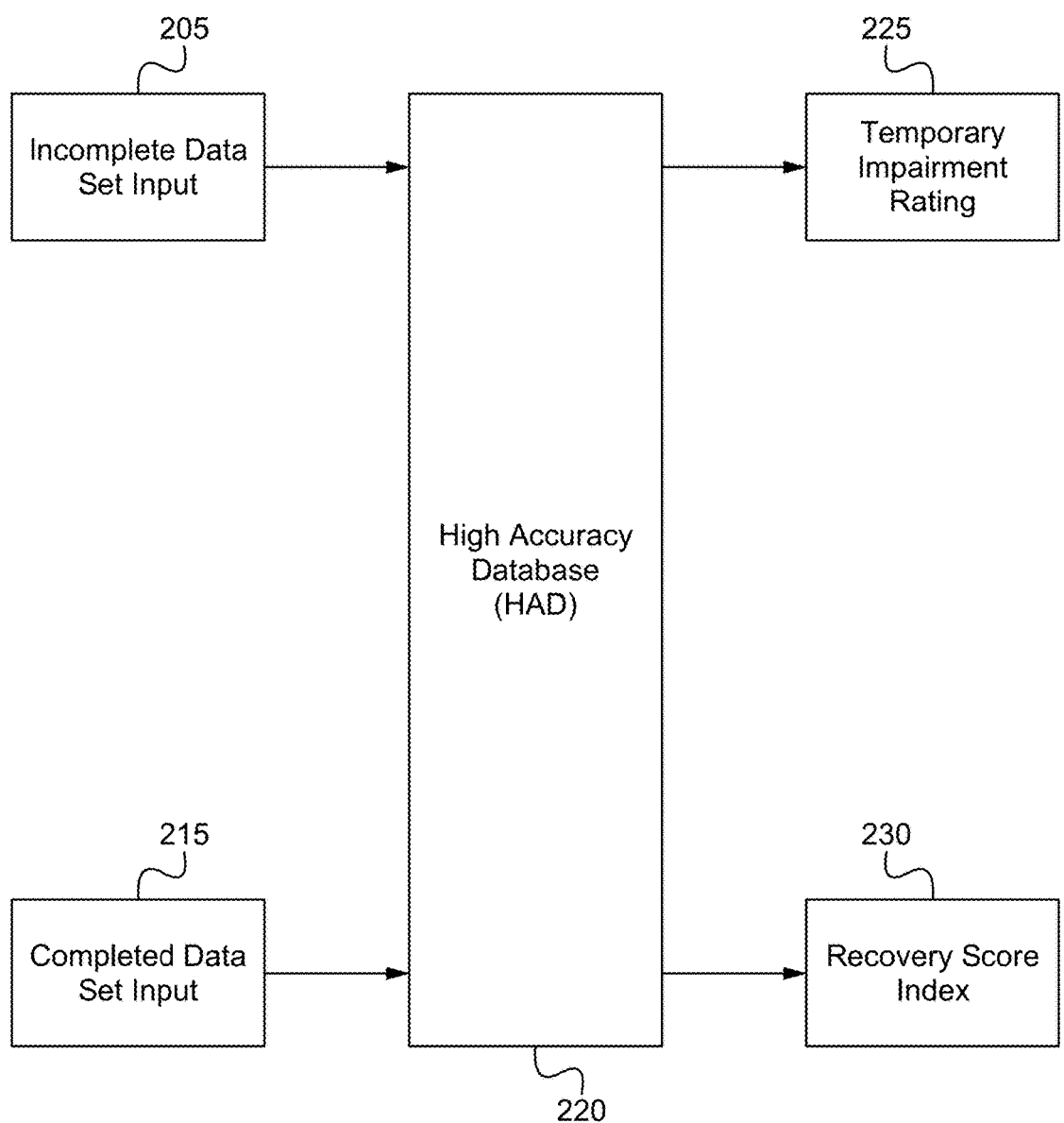
FIG. 2 illustrates system for impairment rating repair in accordance with some embodiments.

FIG. 2 illustrates a system for repairing and/or augmenting an incomplete impairment rating for the impairment repair process. The system 200 comprises an incomplete data set input 205 and a HAD 220. Data from an impairment rating is entered into the incomplete data set input 205 and then is analyzed by the HAD 220. In some embodiments, the data from the impairment rating is input because there is a perceived inaccuracy of the information or the impairment rating process was stopped for some reason and additional data set collection to create an accurate and complete impairment report is not possible. The HAD 220 receives the data from the data input 205 and analyzes the data set to supplement any missing and/or incorrect data based on the injured worker's pathology to fill in the gaps of the impairment rating data entered into the incomplete data set input 205. The HAD 220 is then able to yield at least one of a TIR 225 and a RSI 230, such as described above.

In some embodiments, data entered into the incomplete data set input 205 is analyzed for injury class and type versus one or more ARSs, such as described above, before it is analyzed by the HAD 220. The data can also be analyzed for statistical anomalies. The outputted data can then be compared according similar completed data within the HAD 220. An appropriate prioritization of pathologies and apportionments can also identify the data set for completeness.

As described above, an appropriately complete set for an impairment rating has specific types of sub sets of data, ROM, ADL and others that should be included. If one or more of these data sets are not present, then there are one or more gaps that need to be completed according to the HAD 220. Based on the patient and injury information, the patient is assigned a class standard cohort of similar claims based on historical data of the HAD 220 that is used for statistical data modeling and augmentation of the identified data gaps. The data gaps can be corrected and filled according to data of the HAD 220 which has been reviewed and scrutinized for completeness and class adjusted based on similar prior claims. Using the high accuracy database, a statistical level of confidence for each corrected data gap/result can be assigned. The confidence level is based on an accumulation of the numbers of reports of the injured worker's cohort, such as described above. The more available historical data in the HAD 220, the higher the statistical confidence level.

Data corrected and/or supplemented by the HAD 220 can be coalesced and output to generate a TIR and based on a comparison of the data sets and an original patient chart with the coalesced data, a RSI is also output. The corrected data, the TIR and the RSI are then reviewed and as described above, and if successful then the TIR can be used as a new impairment rating for the injured individual.

As described above, data from an incomplete impairment rating can also undergo an additional analysis. This analysis determines the nature of the examination and where the examination process broke down to identify gaps and discrepancies with typical or normally expected values. This analysis can also identify the presence of potential anomalies within the original data set.

As further shown within FIG. 2, in some embodiments, a completed data set input 215 is utilized to populate the HAD 220 with accurate historical data that is used for statistical data modeling and augmentation of the identified data gaps within the HAD 220. The completed data sets input into the historical database are complete, scrutinized and correct data sets. These data sets can be continuously entered into the HAD 220 so that diverse and consistent data is continuously added to the database 220, which is consistently improved through its use. In some embodiments, the completed data sets are manually entered into the HAD 220. Alternatively, in some embodiments, the database 220 is automatically populated as similar successful worker's compensation claims move toward completion.

Figure 3:
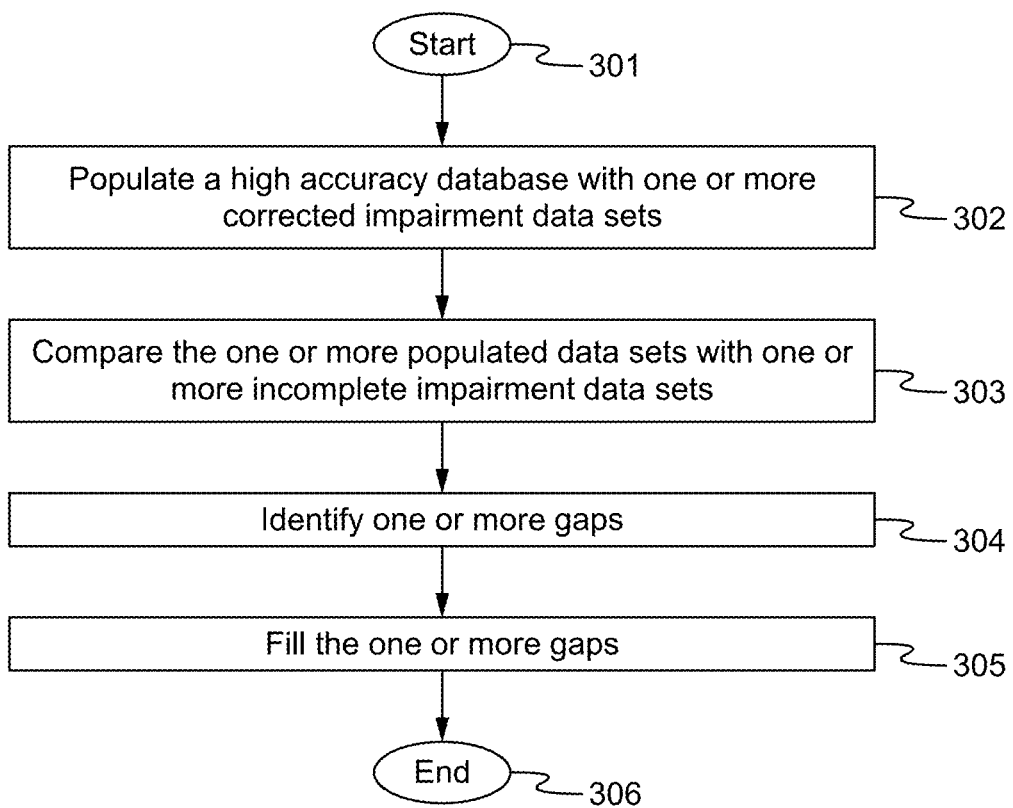
FIG. 3 illustrates a method of impairment rating repair in accordance with some embodiments.

FIG. 3 illustrates a method of impairment rating repair in accordance with further embodiments. The method begins in the step 301. In the step 302, a HAD is populated with complete, scrutinized and correct impairment data sets. Then, in the step 303, the populated data sets are compared to one or more incomplete impairment data sets.

In the step 304, based on the comparison of the populated data sets and the incomplete impairment data sets, one or more data gaps are identified. Then, in the step 305, the data gaps are filled based on the populated data sets to obtain corrected injury impairment data. In some embodiments, at least one of a tentative impairment rating and a recovery score index are outputted based on the corrected injury impairment data. Then, in some embodiments, the tentative impairment rating and the recovery score index are reviewed for accuracy. In some embodiments, if the corrected injury impairment data, the tentative impairment rating and the recovery score index are accurate, the data is transferred to the managed impairment rating process. A statistical level of confidence for the corrected injury impairment data can be assigned for each corrected data gap. In some embodiments, the one or more incomplete impairment data sets are grouped into a cohort based on an injury type and an injury class. The injury type and the injury class can be based on one or more administrative rule sets as applied to the one or more incomplete impairment data sets. The method ends in the step 306.

Figure 4:
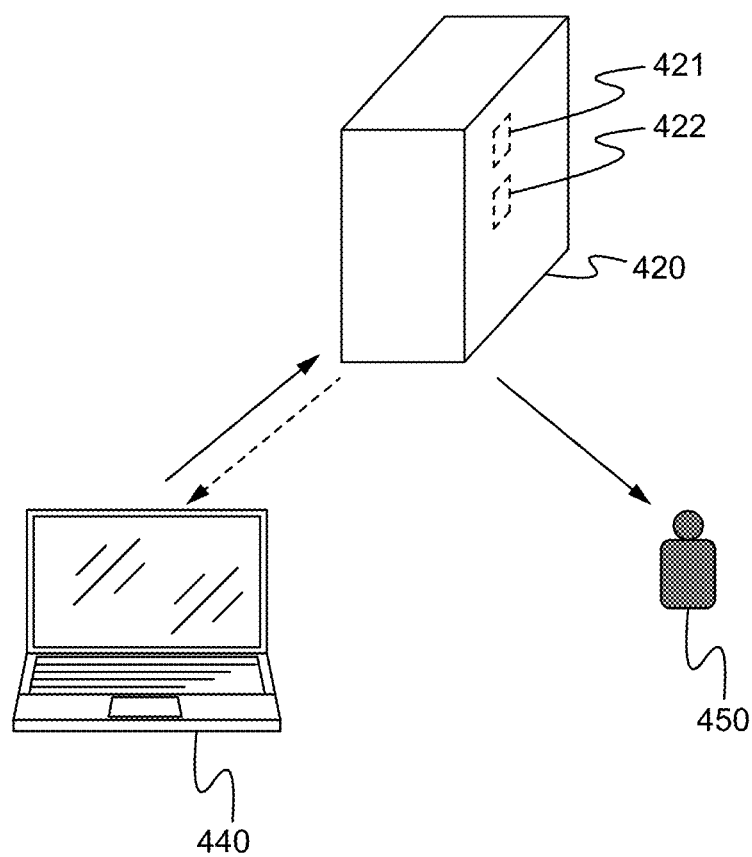
FIG. 4 illustrates a system for impairment rating repair in accordance with some embodiments.

FIG. 4 illustrates a system for repairing and/or augmenting an incomplete impairment rating for the impairment repair process, such as described above. The system 400 comprises a computing device 440 configured for inputting one or more impairment rating data sets, a HAD 420 for receiving the one or more impairment rating data sets and a processor 421 for processing and analyzing the one or more impairment rating data sets. In some embodiments, the one or more impairment rating data sets are automatically uploaded as they are received at the computing device 440.

In some embodiments, the one or more impairment rating data sets comprise one or more incomplete impairment rating data sets, such as described above. The HAD 420 receives the data from the computing device 440 and the processor 421 processes and/or analyzes the data set to supplement any missing and/or incorrect data based on the injured worker's pathology to fill in the gaps of the impairment rating data. As described above, the data received from the computing device 440 can be compared according to similar completed data within the HAD 420 according to the injured worker's pathology. An appropriate prioritization of pathologies and apportionments can also identify the data set for completeness. The HAD 420 receives the data from the computing device 440 and analyzes the data set to supplement any missing and/or incorrect data based on the injured worker's pathology to fill in the gaps of the impairment rating data. In some embodiments, entered data is analyzed for injury class and type versus one or more ARSs, such as described above, before it is processed or analyzed by the HAD 420. The data can also be analyzed for statistical anomalies.

The HAD 420 is then able to yield at least one of a TIR and a RSI, such as described above. The data corrected and/or supplemented by the HAD 420 can be coalesced and output to generate a TIR and based on a comparison of the data sets and an original patient chart with the coalesced data, a RSI is also output. The corrected data, the TIR and the RSI are then reviewed and as described above, and if successful then the TIR can be used as a new impairment rating for the injured individual. In some embodiments, the corrected data, the TIR and the RSI are reviewed by an interested stakeholder 450, such as a QME. Alternatively, in some embodiments, the corrected data, the TIR and the RSI are further processed and reviewed for accuracy by the processor 421 at the HAD 420. An accepted TIR can be used as a new impairment rating and output to the interested stakeholders 450 and/or received by the computing device 440 for use in the MIRP, such as described above.

In some embodiments, the one or more impairment rating data sets inputted into the computing device comprise complete, scrutinized and correct data sets. As described above, the accurate impairment rating data is used for statistical data modeling and augmentation of the identified data gaps within the HAD 420. In some embodiments, the historical accurate impairment data is stored within a memory 422 of the HAD and is accessible by the processor 421 for supplementing any missing and/or incorrect data, such as described above. In some embodiments, these data sets can be continuously stored the HAD 420 so that diverse and consistent data is continuously added to the database 420, which is consistently improved through its use.

Particularly, the HAD is able to store a number and amount of complete, scrutinized and correct data sets for the amount of ARSs and injury types that it would be impossible for a person to analyze the amount of data in the HAD in a meaningful time from home. Indeed, if a person or group of people attempted to perform the claimed analysis the injured worker would likely dies of old age before a resolution to their claim could occur.

In operation, a method of and system for impairment rating repair for the managed impairment rating process. The method and system addresses the circumstance where a lack of confidence in the impairment rating has arrested the process and additional data collection is no longer possible. One or more incomplete data sets are compared to and corrected with a HAD containing reviewed historical impairment data. An analysis of the data outputs a temporary impairment rating and a recovery score index, which yields a corrected and substantially accurate impairment rating report which can be used within the managed impairment repair process as the worker's compensation claim moves toward claim closure.

The unique flexibility of the present invention allows it to be applied from the very early stages through the late stages of the worker's compensation claim process. For example, example 1 shows the present invention applied to a late stage worker's compensation claim to deliver a PR-4 impairment rating with MMI. While example 3, shows the same invention applied to an initial DFR and impairment rating enabling a stakeholder the confidence to restart the claim process.

Particularly, the final product is an impairment rating report for the patient, based on the patient's original claim, with data gaps augment according to one or more algorithms and by using a high accuracy populated database. In this fashion, claims that have been left holder for a long period of time are provided an enhanced impairment rating value and report. Thus, the stakeholders are no longer in limbo and can move toward claim closure. As such the method of and system for impairment rating repair for the managed impairment repair process as described herein has many advantages.

The present invention has been described in terms of specific embodiments incorporating details to facilitate the understanding of the principles of construction and operation of the invention. Such references, herein, to specific embodiments and details thereof are not intended to limit the scope of the claims appended hereto. It will be apparent to those skilled in the art that modifications can be made in the embodiments chosen for illustration without departing from the spirit and scope of the invention.

We claim:
1. A computer implemented method of automatically supplementing data in an incomplete online data set, the method comprising:
  storing, at a storage device of a server computer, historical cohort data that includes a plurality of complete injury impairment rating data sets of a plurality of previous worker's compensation claims, wherein the historical cohort data is continuously updated as one or more injury impairment rating data sets of one or more additional worker's compensation claims are completed;
  receiving, by the server computer from a client computer, encrypted data including a deficient injury impairment rating data set of a pending worker's compensation claim, wherein the deficient injury impairment rating data set for an injury is collected and encrypted by a shell program executing on the client computer and transmitted to the server computer by the shell program to improve computing performance at the server computer, wherein the shell program controls a graphical user interface on the client computer to guide a user using the client computer through prompts to enter data by:
    driving a particular data collection sequence by dynamically generating a set of entry fields that is specific to the pending worker to receive input of observed data set and completed therapies for the injury, wherein driving the specific data collection sequence comprises prompting a plurality of adaptively generated entry fields each based on at least the injury and a range of data entered in a previous entry field, thereby expanding the observed data set such that only necessary data is collected for an impairment rating determination of the pending worker;
    selecting at least one administrative rule set from a plurality of administrative rule sets based on the particular data collection sequence;
      based on the at least one administrative rule set, performing real-time validation calculations of the observed data set as the observed data set is being entered and alerting the treating clinician when the real-time validation calculations indicate that entered input data is outside expected data ranges for the injury;
  decrypting, by the server computer, the encrypted data to obtain the deficient injury impairment rating data set;
  automatically rectifying, by the server computer, the deficient injury impairment rating data set, comprising:

grouping, by the server computer, the pending worker's compensation claim into a cohort of compensation claims based on at least an injury type and an injury class;

accessing, by the server computer, at least a portion of the historical cohort data, wherein the portion of the historical cohort data includes one or more of the plurality of complete injury impairment rating data sets of one or more of the plurality of previous worker's compensation claims that are in the same cohort as the pending worker's compensation claim;

comparing, by the server computer, the deficient injury impairment rating data set to at least the portion of the historical cohort data;

based on the comparison, identifying, by the server computer, one or more data set gaps in the deficient injury impairment rating data set of the pending worker's compensation claim; and applying, by the server computer, statistical models to first data subsets of the portion of the historical cohort data to determine numerical properties from one of the first data subsets, wherein each of the first data subsets corresponds to a respective data set gap of the one or more data set gaps, and based on applying the statistical models, augmenting, by the server computer, the deficient injury impairment data set by filling the one or more data set gaps to obtain a corrected impairment rating data set for the pending worker's compensation claim;

selecting, based on the injury, a particular impairment calculator from a plurality of impairment calculators, wherein accuracy and integrity of the impairment rating determination for an injured worker are verified using a statistical model and pattern recognition, wherein the statistical model evaluates input data for anomalies and outliers, and when no anomalies or outliers are found, the data is received by an impairment calculator, and when the pattern recognition detects data that falls within a specified range, an anomaly response is triggered;

importing data from the corrected impairment rating data set into one or more fields of the particular impairment calculator, wherein the particular impairment calculator applies a plurality of criteria for the injury, as defined by the at least one administrative rule sets, to determine an impairment rating for the injury;

generating, by the server computer, a report based on the corrected impairment rating data set and the impairment rating;

in response to generating the report, restarting a managed impairment rating process for closure of the pending worker's compensation claim; and updating the historical cohort data based on the corrected impairment rating data set.

2. The method of claim 1, wherein the method further comprises assigning a statistical level of confidence for each filled data set gap in the corrected impairment rating data set.

3. The method of claim 1, wherein the injury type and the injury class are based on the one or more administrative rule sets as applied to the deficient injury impairment rating data set.

4. The method of claim 1, wherein the method further comprises identifying a break down in the impairment rating process of the pending worker's compensation claim, from the deficient injury impairment rating data set.

5. A method of impairment rating repair comprising:

populating a storage device of a server computer with historical cohort data comprising a plurality of complete impairment rating data sets of a plurality of previous worker's compensation claims, wherein the storage device is automatically populated as one or more injury impairment rating data sets of one or more additional worker's compensation claims are completed;

receiving, by the server computer from a client computer, encrypted data including a deficient injury impairment rating data set of a pending worker's compensation claim, wherein the deficient injury impairment rating data set for an injury is collected and encrypted by a shell program executing on the client computer and transmitted to the server computer by the shell program to improve computing performance at the server computer, wherein the shell program controls a graphical user interface on the client computer to guide a user using the client computer through prompts to enter data by:

driving a particular data collection sequence by dynamically generating a set of entry fields that is specific to the pending worker to receive input of observed data set and completed therapies for the injury, wherein driving the specific data collection sequence comprises prompting a plurality of adaptively generated entry fields each based on at least the injury and a range of data entered in a previous entry field, thereby expanding the observed data set such that only necessary data is collected for an impairment rating determination of the pending worker;

selecting at least one administrative rule set from a plurality of administrative rule sets based on the particular data collection sequence;

based on the at least one administrative rule set, performing real-time validation calculations of the observed data set as the observed data set is being entered and alerting the treating clinician when the real-time validation calculations indicate that entered input data is outside expected data ranges for the injury;

decrypting, by the server computer, the encrypted data to obtain the deficient injury impairment rating data set;

automatically rectifying, by the server computer, the deficient injury impairment rating data set, comprising:

grouping, by the server computer, the pending worker's compensation claim into a cohort of compensation claims based on at least an injury type and an injury class;

accessing, by the server computer, at least a portion of the historical cohort data, wherein the portion of the historical cohort data includes one or more of the plurality of complete injury impairment rating data sets of one or more of the plurality of previous worker's compensation claims that are in the same cohort as the pending worker's compensation claim;

comparing, by the server computer, the deficient injury impairment rating data set to at least the portion of the historical cohort data;

based on the comparison, identifying, by the server computer, one or more data set gaps in the deficient injury impairment rating data set of the pending worker's compensation claim; and applying, by the server computer, statistical models to first data subsets of the portion of the historical cohort data to determine numerical properties from one of the first data subsets, wherein each of the first data subsets corresponds to a respective data set gap of the one or more data set gaps, and based on applying the statistical models, augmenting, by the server computer, the deficient injury impairment data set by filling the one or more data set gaps to obtain a corrected impairment rating data set for the pending worker's compensation claim;

selecting, based on the injury, a particular impairment calculator from a plurality of impairment calculators, wherein accuracy and integrity of the impairment rating determination for an injured worker are verified using a statistical model and pattern recognition, wherein the statistical model evaluates input data for anomalies and outliers, and when no anomalies or outliers are found, the data is received by an impairment calculator, and when the pattern recognition detects data that falls within a specified range, an anomaly response is triggered;

importing data from the corrected impairment rating data set into one or more fields of the particular impairment calculator, wherein the particular impairment calculator applies a plurality of criteria for the injury, as defined by the at least one administrative rule sets, to determine an impairment rating for the injury;

generating, by the server computer, a report based on the corrected impairment rating data set and the impairment rating; and in response to generating the report, restarting a managed impairment rating process for closure of the pending worker's compensation claim.

6. The method of claim 5, wherein the method further comprises assigning a statistical level of confidence for each filled data set gap in the corrected impairment rating data set.

7. The method of claim 5, wherein the injury type and the injury class are based on the one or more administrative rule sets as applied to the deficient injury impairment rating data set.

8. The method of claim 5, wherein the method further comprises identifying a break down in the impairment rating process of the pending worker's compensation claim.

9. The method of claim 5, wherein the corrected impairment rating data set is a complete set for the impairment rating, wherein the complete set includes a plurality of subsets, wherein the plurality of subsets include a range of motion (ROM) data and activities of daily living (ADL) data.

10. The method of claim 5, the method further comprises updating the historical cohort impairment data based on the corrected impairment rating data set of the pending worker's compensation claim.

11. A computing system comprising:
one more computer systems comprising one or more hardware processors and storage media; and
instructions stored in the storage media and which, when executed by the computing system, cause the computing system to perform:
storing, at a storage device of a server computer, historical cohort data that includes a plurality of complete injury impairment rating data sets of a plurality of previous worker's compensation claims, wherein the historical cohort data is continuously updated as one or more injury impairment rating data sets of one or more additional worker's compensation claims are completed;
receiving, by the server computer from a client computer, encrypted data including a deficient injury impairment rating data set of a pending worker's compensation claim, wherein the deficient injury impairment rating data set for an injury is collected and encrypted by a shell program executing on the client computer and transmitted to the server computer by the shell program to improve computing performance at the server computer, wherein the shell program controls a graphical user interface on the client computer to guide a user using the client computer through prompts to enter data by:
driving a particular data collection sequence by dynamically generating a set of entry fields that is specific to the pending worker to receive input of observed data set and completed therapies for the injury, wherein driving the specific data collection sequence comprises prompting a plurality of adaptively generated entry fields each based on at least the injury and a range of data entered in a previous entry field, thereby expanding the observed data set such that only necessary data is collected for an impairment rating determination of the pending worker;
selecting at least one administrative rule set from a plurality of administrative rule sets based on the particular data collection sequence;
based on the at least one administrative rule set, performing real-time validation calculations of the observed data set as the observed data set is being entered and alerting the treating clinician when the real-time validation calculations indicate that entered input data is outside expected data ranges for the injury;
decrypting, by the server computer, the encrypted data to obtain the deficient injury impairment rating data set;
automatically rectifying, by the server computer, the deficient injury impairment rating data set, comprising:
grouping, by the server computer, the pending worker's compensation claim into a cohort of compensation claims based on at least an injury type and an injury class;
accessing, by the server computer, at least a portion of the historical cohort data, wherein the portion of the historical cohort data includes one or more of the plurality of complete injury impairment rating data sets of one or more of the plurality of previous worker's compensation claims that are in the same cohort as the pending worker's compensation claim;
comparing, by the server computer, the deficient injury impairment rating data set to at least the portion of the historical cohort data; based on the comparison, identifying, by the server computer, one or more data set gaps in the deficient injury impairment rating data set of the pending worker's compensation claim; and
applying, by the server computer, statistical models to first data subsets of the portion of the historical cohort data to determine numerical properties from one of the first data subsets, wherein each of the first data subsets corresponds to a respective data set gap of the one or more data set gaps, and based on applying the statistical models, augmenting, by the server computer, the deficient injury impairment data set by filling the one or more data set gaps to obtain a corrected impairment rating data set for the pending worker's compensation claim;

selecting, based on the injury, a particular impairment calculator from a plurality of impairment calculators, wherein accuracy and integrity of the impairment rating determination for an injured worker are verified using a statistical model and pattern recognition, wherein the statistical model evaluates input data for anomalies and outliers, and when no anomalies or outliers are found, the data is received by an impairment calculator, and when the pattern recognition detects data that falls within a specified range, an anomaly response is triggered;

importing data from the corrected impairment rating data set into one or more fields of the particular impairment calculator, wherein the particular impairment calculator applies a plurality of criteria for the injury, as defined by the at least one administrative rule sets, to determine an impairment rating for the injury;

generating, by the server computer, a report based on the corrected impairment rating data set and the impairment rating;

in response to generating the report, restarting a managed impairment rating process for closure of the pending worker's compensation claim; and updating the historical cohort data based on the corrected impairment rating data set.

12. The system of claim 11, wherein the instructions, when executed by the computing system, cause the computing system to further perform assigning a statistical level of confidence for each filled data set gap in the corrected impairment rating data set.

13. The system of claim 11, wherein the injury type and the injury class are based on the one or more administrative rule sets as applied to the deficient injury impairment rating data set.

14. The system of claim 11, wherein the instructions, when executed by the computing system, cause the computing system to further perform identifying a break down in the impairment rating process of the pending worker's compensation claim, from the deficient injury impairment rating data set.

15. A computing system comprising:
one more computer systems comprising one or more hardware processors and storage media; and
instructions stored in the storage media and which, when executed by the computing system, cause the computing system to perform:
populating a storage device of a server computer with historical cohort data comprising a plurality of complete impairment rating data sets of a plurality of previous worker's compensation claims, wherein the storage device is automatically populated as one or more injury impairment rating data sets of one or more additional worker's compensation claims are completed;
receiving, by the server computer from a client computer, encrypted data including a deficient injury impairment rating data set of a pending worker's compensation claim, wherein the deficient injury impairment rating data set for an injury is collected and encrypted by a shell program executing on the client computer and transmitted to the server computer by the shell program to improve computing performance at the server computer, wherein the shell program controls a graphical user interface on the client computer to guide a user using the client computer through prompts to enter data by:
driving a particular data collection sequence by dynamically generating a set of entry fields that is specific to the pending worker to receive input of observed data set and completed therapies for the injury, wherein driving the specific data collection sequence comprises prompting a plurality of adaptively generated entry fields each based on at least the injury and a range of data entered in a previous entry field, thereby expanding the observed data set such that only necessary data is collected for an impairment rating determination of the pending worker;
selecting at least one administrative rule set from a plurality of administrative rule sets based on the particular data collection sequence;
based on the at least one administrative rule set, performing real-time validation calculations of the observed data set as the observed data set is being entered and alerting the treating clinician when the real-time validation calculations indicate that entered input data is outside expected data ranges for the injury;
decrypting, by the server computer, the encrypted data to obtain the deficient injury impairment rating data set;
automatically rectifying, by the server computer, the deficient injury impairment rating data set, comprising:
grouping, by the server computer, the pending worker's compensation claim into a cohort of compensation claims based on at least an injury type and an injury class;
accessing, by the server computer, at least a portion of the historical cohort data, wherein the portion of the historical cohort data includes one or more of the plurality of complete injury impairment rating data sets of one or more of the plurality of previous worker's compensation claims that are in the same cohort as the pending worker's compensation claim;
comparing, by the server computer, the deficient injury impairment rating data set to at least the portion of the historical cohort data;
based on the comparison, identifying, by the server computer, one or more data set gaps in the deficient injury impairment rating data set of the pending worker's compensation claim; and
applying, by the server computer, statistical models to first data subsets of the portion of the historical cohort data to determine numerical properties from one of the first data subsets, wherein each of the first data subsets corresponds to a respective data set gap of the one or more data set gaps, and based on applying the statistical models, augmenting, by the server computer, the deficient injury impairment data set by filling the one or more data set gaps to obtain a corrected impairment rating data set for the pending worker's compensation claim;
selecting, based on the injury, a particular impairment calculator from a plurality of impairment calculators, wherein accuracy and integrity of the impairment rating determination for an injured worker are verified using a statistical model and pattern recognition, wherein the statistical model evaluates input data for anomalies and outliers, and when no anomalies or outliers are found, the data is received by an impairment calculator, and when the pattern recognition detects data that falls within a specified range, an anomaly response is triggered;

importing data from the corrected impairment rating data set into one or more fields of the particular impairment calculator, wherein the particular impairment calculator applies a plurality of criteria for the injury, as defined by the at least one administrative rule sets, to determine an impairment rating for the injury;

generating, by the server computer, a report based on the corrected impairment rating data set and the impairment rating; and in response to generating the report, restarting a managed impairment rating process for closure of the pending worker's compensation claim.

16. The system of claim 15, wherein the instructions, when executed by the computing system, cause the computing system to further perform assigning a statistical level of confidence for each filled data set gap in the corrected impairment rating data set.

17. The system of claim 15, wherein the injury type and the injury class are based on the one or more administrative rule sets as applied to the deficient injury impairment rating data set.

18. The system of claim 15, wherein the instructions, when executed by the computing system, cause the computing system to further perform identifying a break down in the impairment rating process of the pending worker's compensation claim.

19. The system of claim 15, wherein the corrected impairment rating data set is a complete set for an impairment rating, wherein the complete set includes a plurality of subsets, wherein the plurality of subsets include a range of motion (ROM) data and activities of daily living (ADL) data.

20. The system of claim 15, wherein the instructions, when executed by the computing system, cause the computing system to further perform updating the historical cohort impairment data with the corrected impairment rating data set of the pending worker's compensation claim.

* * * * *